United States Patent
Pfaendner et al.

(10) Patent No.: US 7,253,232 B2
(45) Date of Patent: Aug. 7, 2007

(54) THERMOPLASTIC COMPOSITIONS WITH ENHANCED MELT FLOW AND COMPATIBILITY

(75) Inventors: Rudolf Pfaendner, Rimbach (DE); Jochen Fink, Nussloch (DE); Wiebke Wunderlich-Wippert, Lörrach (DE); Andreas Kramer, Meyriez (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 170 days.

(21) Appl. No.: 10/527,610

(22) PCT Filed: Sep. 18, 2003

(86) PCT No.: PCT/EP03/10393

§ 371 (c)(1),
(2), (4) Date: Mar. 11, 2005

(87) PCT Pub. No.: WO2004/029156

PCT Pub. Date: Apr. 8, 2004

(65) Prior Publication Data

US 2005/0288435 A1    Dec. 29, 2005

(30) Foreign Application Priority Data

Sep. 26, 2002   (EP)   .................. 02405832

(51) Int. Cl.
*C08L 83/10*   (2006.01)
*C08L 53/00*   (2006.01)

(52) U.S. Cl. .................. 525/69; 525/88; 525/92 B; 525/92 G; 525/92 D; 525/92 E

(58) Field of Classification Search .................. 525/99, 525/66, 88, 92 B, 92 D, 92 E, 92 G
See application file for complete search history.

(56) References Cited

U.S. PATENT DOCUMENTS

| | | | |
|---|---|---|---|
| 3,691,257 A | 9/1972 | Kendrick et al. | ........... 260/827 |
| 4,079,098 A * | 3/1978 | Rossmy et al. | ............. 525/102 |
| 5,627,248 A | 5/1997 | Koster et al. | ................ 526/217 |
| 5,728,469 A | 3/1998 | Mann et al. | ................ 428/418 |
| 6,331,589 B1 | 12/2001 | Hoxmeier | .................. 525/54.3 |

FOREIGN PATENT DOCUMENTS

| | | |
|---|---|---|
| DE | 3441239 | 5/1986 |
| WO | 96/39349 | 12/1996 |
| WO | 99/46261 | 9/1999 |
| WO | 02/48205 | 6/2002 |

OTHER PUBLICATIONS

English language abstract for DE 3441239 (1986).
Patent Abstracts of Japan Publications No. 2002030106 (2002).

* cited by examiner

*Primary Examiner*—Jeffrey Mullis
(74) *Attorney, Agent, or Firm*—Tyler A. Stevenson

(57) ABSTRACT

The instant invention relates to a composition of a thermoplastic polymer and a triblock-copolymer or grafted comb copolymer, with enhanced melt flow during processing. Further aspects of the invention are the triblock-copolymers or grafted comb polymers itself, a method for their production and their use as compatibilizers and meltflow enhancing additives. Yet another aspect of the invention are functional alkoxyamines, which are useful for the preparation of the triblock-copolymers or grafted comb polymers.

8 Claims, No Drawings

THERMOPLASTIC COMPOSITIONS WITH ENHANCED MELT FLOW AND COMPATIBILITY

The instant invention relates to a composition of a thermoplastic polymer and a triblock-copolymer or grafted comb copolymer, with enhanced melt flow during processing. Further aspects of the invention are the triblock-copolymers or grafted comb polymers itself, a method for their production and their use as compatibilizers and meltflow enhancing additives. Yet another aspect of the invention are functional alkoxyamines, which are useful for the preparation of the triblock-copolymers or grafted comb polymers.

Productivity of formgiving and compounding processes of thermoplastic materials, such as extrusion or injection molding is often related to the melt viscosity of polymers, i.e. by lowering the melt viscosity, throughput can be increased and cycle times and energy consumption can be considerably reduced. The melt viscosity is related to the molecular weight of the polymer. Increasing the molecular weight leads to an increase in melt viscosity.

On the other hand it is not possible to reduce the molecular weight in order to gain a reduced melt viscosity, since other important properties of polymers such as mechanical strength depend also on the molecular weight of the polymer. It is therefore a clear request of the plastic and converting industry for a material combination of low melt viscosity (or enhanced melt flow) without influence on other material properties, such as mechanical strength or transparency.

Additives fulfilling at least partially the aformentioned requirements in certain polymers are known and are often referred to as lubricants (e.g. polyethylene, polytetrafluoroethylene, amide waxes) and/or processing aids (fluoropolymers, silicones). However, the use of these additives results often in blooming, tool deposits, reduced transparency and "fatty" surface aspect due to their inherent incompatibility with the parent polymer.

For example U.S. Pat. No. 6,331,589 discloses diblock-copolymers containing one polysiloxane segment and a polystyrene or polyethylene segment as melt flow enhancing additive.

The present invention provides a composition of a thermoplastic polymer and a triblock-copolymer, which is preferably prepared via controlled radical polymerization. The triblock-copolymer has an improved compatibility with the thermoplastic polymer and enhances the melt flow of the thermoplastic polymer. Mechanical properties, optical aspect, surface characteristics and color of the parent polymer are essentially not affected.

One aspect of the invention is a composition comprising

A) a thermoplastic polymer and

B1) a triblock-copolymer of the formula B-C-B; or

B2) a graft copolymer wherein a polymer block B is grafted onto a polymer C to form a comb copolymer of idealized formula C-B(n) wherein n is greater than 2;

wherein the polymer block B is compatible to the thermoplastic polymer A); and the polymer block C has a glass transition temperature of at least 20° K. below the glass transition temperature of the thermoplastic polymer A);

and the average molecular weight $M_w$ of the triblock-copolymer B1) or grafted comb copolymer B2) is below 50 000.

In general the triblock-copolymer is preferred.

The polydispersity index of the triblock-copolymer and the grafted comb copolymer is for example between 1.0 and 5.0, preferably between 1.1 and 3.0 and in particular between 1.1 and 2.0.

Suitable thermoplastic polymers are mentioned below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned In 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EM and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly($\alpha$-methylstyrene).

6. Aromatic homopolymers and copolymers derived from vinyl aromatic monomers including styrene, $\alpha$-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.
20. Polyketones.
21. Polysulfones, polyether sulfones and polyether ketones.
22. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preferably the thermoplastic polymer A is selected from the group consisting of polyethylene, polypropylene, polystyrene, polyacrylate, polymethacrylate, polyvinylchloride, polyphenylene-oxide, polyvinylacetate, polyamide and polyester.

In particular the thermoplastic polymer A is selected from the group consisting of polyethylene, polypropylene and polystyrene.

For example the polymer block C is selected from the group consisting of poly-n-butylacrylate, polyisoprene, polybutadiene, polyethylacrylate, and polysiloxane.

For instance the polymer block B is selected from the group consisting of polyisoprene, poly-butadiene, polystyrene polymethacrylate and polyacrylate.

In a typical embodiment of the invention the thermoplastic polymer A and the triblock-copolymer B-C-B are polystyrene polystyrene-poly-n-butylacrylate-polystyrene, polystyrene polystyrene-polyisoprene-polystyrene, polystyrene polystyrene-polybutadiene-polystyrene, polystyrene polystyrene-polysiloxane-polystyrene, polystyrene polystyrene-polyethylacrylate-polystyrene, polyethylene polyisoprene-polysiloxane-polyisoprene, polypropylene polyisoprene-polysiloxane-polyisoprene, polymethylmethacrylate polymethylacrylate-polysiloxane-polymethylacrylate, polyamide polyethylacrylate-polysiloxane-polyethylacrylate, polyester polyethylacrylate-polysiloxane-polyethylacrylate, polyvinylchloride polyethylacrylate-polysiloxane-polyethylacrylate, polyvinylchloride poly-n-butylacrylate-polysiloxane-poly-n-butylacrylate, polyphenyleneoxide polystyrene-polysiloxane-polystyrene or polyvinylacetate polymethylacrylate-polysiloxane-polymethylacrylate.

For example the glass transition temperature of the polymer block C is 50° K. below the glass transition temperature of the thermoplastic polymer A.

Preferably the average molecular weight $M_w$ of the triblock-copolymer or graft-copolymer is below 30000.

Each individual block has for example an average molecular weight $M_w$ of 2000 to 20000, in particular from 2000 to 10000 with the proviso that the total is below 50000, preferably below 30000.

Particularly the polymer block C is a polysiloxane.

Typically the triblock-copolymer or graft graft-copolymer is present in an amount of from 0.1 to 10%, preferably of from 0.5 to 5% and in particular of from 0.5 to 3% by weight, based on the weight of the thermoplastic polymer A).

The composition may contain further additives, such as for example light stabilizers, UV-absorbers, processing stabilizers, pigments or dyes and so on. Examples are given below.

1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzoate malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4- hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]—, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl] benzotriazole.

2.2. 2-Hydroxybenzorphenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2, 2,6,6-tetra-methyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperldine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7, 7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis (4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis (2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2, 6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4, 6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethyl-phenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1- oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thlopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl)phosphite (Irgafos®168, Ciba-Geigy), tris(nonylphenyl)phosphite,

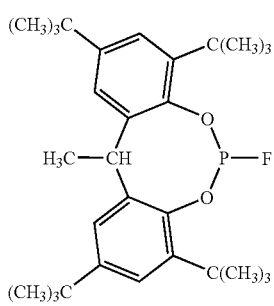
(A)

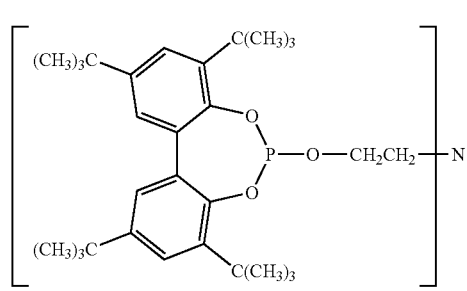
(B)

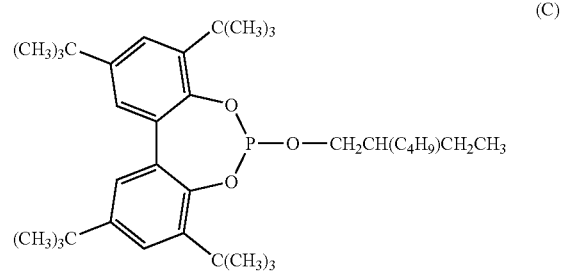
(C)

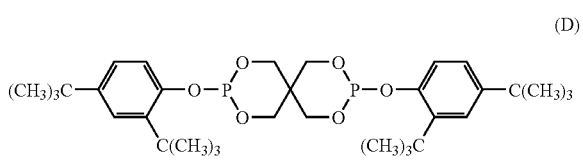
(D)

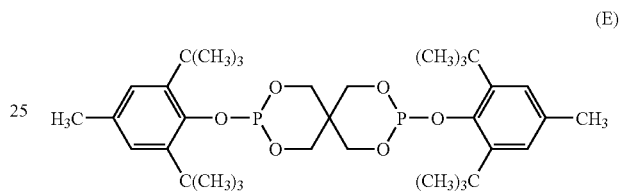
(E)

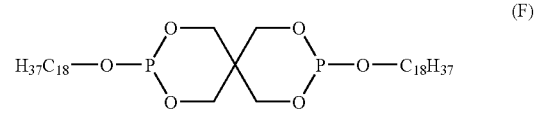
(F)

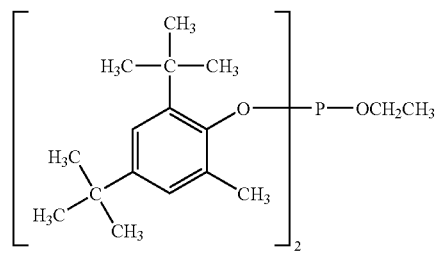
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydrox-ylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptynitrone, N-lauryl-alpha-undecylnitrone, N-tetradecyl-alpha-tridecylnitrone, N-hexadecyl-alpha-pentadecyinitrone, N-octadecyl-alpha-heptadecyinitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyidibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The triblock-copolymer or grafted comb copolymer of the invention and optional further components may be added to the thermoplastic polymer material individually or mixed with one another. If desired, the individual components can be mixed with one another before incorporation into the polymer for example by dry blending, compaction or in the melt.

The incorporation of the triblock-copolymer or grafted comb copolymer of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additve or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion, Vol. 1 Grundlagen*, Editors F. Hensen, W. Knappe, H. Potente, 1989, pp. 3-7, ISBN:3-446-14339-4 (*Vol. 2 Extrusionsanlagen* 1986, ISBN 3-446-14329-7).

For example, the screw length is 1-60 screw diameters, preferably 35-48 screw diameters. The rotational speed of the screw is preferably 10-600 rotations per minute (rpm), very particularly preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components are added, these can be premixed or added individually.

The triblock-copolymer or grafted comb copolymer of the invention and optional further additives can also be added to the polymer in the form of a masterbatch ("concentrate") which contains the components in a concentration of, for example, about 1% to about 40% and preferably 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Incorporation can take place prior to or during the shaping operation, or by applying the dissolved or dispersed compound to the polymer, with or without subsequent evaporation of the solvent.

The materials containing the triblock-copolymer or grafted comb copolymer of the invention described herein can be used for the production of moldings, rotomolded articles, injection molded articles, blow molded articles, films, tapes, mono-filaments, fibers, nonwovens, profiles, adhesives or putties, surface coatings and the like.

The triblock-copolymer can be prepared according to standard polymerization methods, such as for example anionic polymerization of the individual blocks. Such a method is for example described for diblock-copolymers of polyethylene and polysiloxane in U.S. Pat. No. 6,331,589.

The synthesis of triblock copolymers via anionic polymerization is well known and e.g. described in Houben-Weyl, Methoden der organischen Chemie, Band E20, page 132, Stuttgart 1987.

Synthesis can be performed either in a 3 step process, where the first monomer, is initiated e.g. by 2-butyllithium (block B), followed by addition of the $2^{nd}$ monomer (resulting in B-C block) and finally the first monomer is added again (resulting in B-C-B). A 2 step process is achieved by using a bifunctional initiator e.g. Naphthalin sodium THF complex, where the block C is synthesized first, followed by addition of the second monomer, whereas both B blocks are formed at the same time. A further possibility of a 2 step process is the initiation of the first monomer by a monofunctional initiator, followed by the second monomer and coupling of the living chain ends by addition of a coupling agent e.g. α,ω-dichlorocompounds or dichlordimethylsilane. Comb polymers via anionic polymerization can be synthesized by metalization of a polymer chain e.g. polybutadiene with butyl-lithium-1,2-bis(dimethylamino)ethan complex, followed by initiation of the second monomer from the metal (Li) containing polymer backbone.

A further method to synthesize the B-C-B block copolymers is by condensation reaction between functional endgroups of indiviual blocks. For example a dimethyl-amino-terminated polysiloxane at both ends (block C) can be reacted with a hydroxy-terminated block B by condensation reaction (see e.g. Houben Weyl Vol. 20 E, page 2232).

In a preferred method the block polymerization is carried out in the presence of nitroxyl mediated radical polymerization in a similar way as described for diblocks in Polymer Preprints Vol 40(2), 1999, pages 370-371.

The synthesis of B-C blockcopolymers via nitroxyl mediated polymerization is carried out as described e.g. in WO 02/48205.

Synthesis of B-C-B blockcopolymers via nitroxyl mediated polymerization can be synthesized by subsequent block copolymer formation, starting with a monomer B, followed by a monomer C and again followed by a monomer B. Another possibility is to use a bifunctional nitroxylinitiator as described for example in U.S. Pat. No. 5,627,248, polymerizing first a monomer C, followed by the monomer B which is in this case growing on both ends, resulting in a B-C-B structure.

A further aspect of the invention is therefore a process for the preparation of a triblock-copolymer or graft-copolymer via controlled free radical polymerization comprising the steps of a) reacting a polysiloxane, in the presence of a functional alkoxyamine of formula (I)

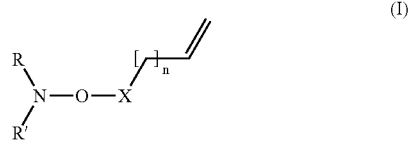

(I)

under hydrosylilation conditions and b) reacting the resulting alkoxyamine terminated polysiloxane with an ethylenically unsaturated monomer at a temperature between 60 and 160° C., wherein X represents a group having at least one carbon atom and is such that the free radical

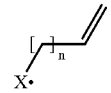

is capable of initiating polymerization of ethylenically unsaturated monomers, n is a number from 0-18;

R and R' are independently tertiary bound $C_4$-$C_{28}$alkyl groups which are unsubstituted or substitituted by one or more electron withdrawing groups or by phenyl; or R and R' together form a 5 or 6 membered heterocyclic ring which is substituted at least by 4 $C_1$-$C_4$alkyl groups and which may be interrupted by a further nitrogen or oxygen atom.

Suitable nitroxyl radicals as precursors for the compounds of formula I are known and disclosed in the following documents.

U.S. Pat. No. 5,322,912 to Georges et al. issued Jun. 21, 1994 discloses a polymerization process using a free radical initiator, a polymerizable monomer compound and a stable free radical agent of the basic structure R'R"N—O● for the synthesis of homopolymers and block copolymers which are terminated by the nitroxyl radical.

More recently further nitroxyl radicals and nitroxyl ethers have been described. WO 98/13392 for example describes open chain alkoxyamine compounds, which have a symmetrical substitution pattern and are derived from NO gas or from nitroso compounds.

WO 96/24620 describes a polymerization process in which very specific stable free radical agents are used, such as for example

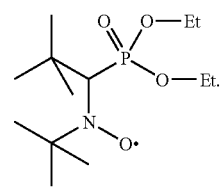

WO 98/30601 discloses specific nitroxyls based on imidazolidinons.

WO 98/44008 discloses specific nitroxyls based on morpholinones, piperazinones and piperazindiones.

The preparation of open chain nitroxyl radicals is for example also described in WO 99/03894 or in WO 00/07981. Nitroxyl radicals based on tetraalkyl piperidine are for example described in GB 2 335 1290 or in GB 2 361 235. Further heterocyclic nitroxyl radicals are described in GB 2 342 649.

These prior art nitroxyl radicals are all suitable precursors for the instant functional alkoxyamines. They may be prepared in analogy to the epoxy functionalized alkoxyamines disclosed in WO 02/48109.

In principal a hydroxy functional alkoxyamine is reacted with a halogen alkene having the double bond as terminal group, such as for example allyl bromide.

Preferably the functional alkoxyamine is of formula (II)

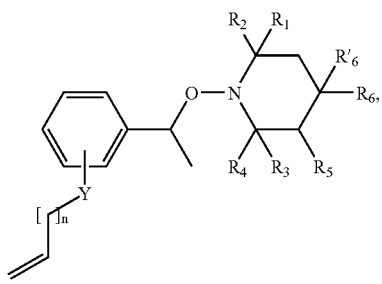

wherein

Y is a direct bond, O, NH, C(O)O or S;

n is a a number from 0-18.

$R_1$, $R_2$, $R_3$ and $R_4$ are independently of each other $C_1$-$C_4$alkyl;

$R_5$ is hydrogen or $C_1$-$C_4$alkyl;

$R'_6$ is hydrogen and $R_6$ is H, $OR_{10}$, $NR_{10}R_{11}$, —O—C(O)—$R_{10}$ or $NR_{11}$—C(O)—$R_{10}$;

$R_{10}$ and $R_{11}$ independently are hydrogen, $C_1$-$C_{18}$alkyl, $C_2$-$C_{18}$alkenyl, $C_2$-$C_{18}$alkinyl or $C_2$-$C_{18}$alkyl which is substituted by at least one hydroxy group or, if $R_6$ is $NR_{10}R_{11}$, taken together, form a $C_2$-$C_{12}$alkylene bridge or a $C_2$-$C_{12}$-alkylene bridge interrupted by at least one O atom; or $R_6$ and $R'_6$ together are both hydrogen, a group =O or =N—O—$R_{20}$ wherein $R_{20}$ is H, straight or branched $C_1$-$C_{18}$alkyl, $C_3$-$C_{18}$alkenyl or $C_3$-$C_{18}$alkinyl, which may be unsubstituted or substitued, by one or more OH, $C_1$-$C_8$alkoxy, carboxy, $C_1$-$C_8$alkoxycarbonyl;

$C_5$-$C_{12}$cycloalkyl or $C_5$-$C_{12}$cycloalkenyl;

phenyl, $C_7$-$C_9$phenylalkyl or naphthyl which may be unsubstituted or substituted by one or more $C_1$-$C_8$alkyl, halogen, OH, $C_1$-$C_8$alkoxy, carboxy, $C_1$-$C_8$alkoxycarbonyl;

—C(O)—$C_1$-$C_{36}$alkyl, or an acyl moiety of a α,β-unsaturated carboxylic acid having 3 to 5 carbon atoms or of an aromatic carboxylic acid having 7 to 15 carbon atoms;

—$SO_3^-Q^+$, —$PO(O^-Q^+)_2$, —$P(O)(OR_2)_2$, —$SO_2)_2$—$R_2$, —CO—NH—$R_2$, —$CONH_2$, $COOR_2$, or $Si(Me)_3$, wherein $Q^+$ is $H^+$, ammonium or an alkali metal cation; or $R_6$ and $R_6'$ are independently —O—$C_1$-$C_{12}$alkyl, —O—$C_3$-$C_{12}$alkenyl, —O—$C_3$-$C_{12}$alkinyl, —O—$C_5$-$C_8$cycloalkyl, —O-phenyl, —O-naphthyl, —O—$C_7$-$C_9$phenylalkyl; or $R_6$ and $R'_6$ together form one of the bivalent groups —O—C($R_{21}$)($R_{22}$)—CH($R_{23}$)—O—, —O—CH($R_{21}$)—$CH_{22}$—C($R_{22}$)($R_{23}$)—O—, —O—CH($R_{22}$)—$CH_2$—C($R_{21}$)($R_{23}$)—O—, —O—$CH_2$—C($R_{21}$)($R_{22}$)—CH($R_{23}$)—O—, —O-o-phenylene-O—, —O—-1,2-cyclohexyliden-O—, —O---$CH_2$—CH=CH—$CH_2$—O— or

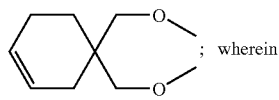 ; wherein $R_{21}$ is hydrogen, $C_1$-$C_{12}$alkyl, COOH, COO—($C_1$-$C_{12}$) alkyl or $CH_2OR_{24}$;

$R_{22}$ and $R_{23}$ are independently hydrogen, methyl ethyl, COOH or COO—($C_1$-$C_{12}$)alkyl; and $R_{24}$ is hydrogen, $C_1$-$C_{12}$alkyl, benzyl, or a monovalent acyl residue derived from an aliphatic, cycloaliphatic or aromatic monocarboxylic acid having up to 18 carbon atoms.

Preferably Y is O and n is a number from 1-4.

$C_1$-$C_{18}$alkyl can be linear or branched. Examples are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl or octadecyl. Where up to $C_{3-6}$alkyl is possible, $C_1$-$C_{18}$alkyl is preferred. Alkyl substituted by a group —COOH is for example $CH_2$—COOH, $CH_2$—$CH_2$—COOH, $(CH_2)_3$—COOH or $CH_2$—CHCOOH—$CH_2$—$CH_3$ Hydroxyl- or alkoxycarbonyl substituted $C_1$-$C_{18}$alkyl can be, for example, 2-hydroxyethyl, 2-hydroxypropyl, methoxycarbonylmethyl or 2-ethoxycarbonylethyl.

Alkenyl having from 2 to 18 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl, isododecenyl.

Alkinyl having from 2 to 18 carbon atoms is a branched or unbranched radical, for example propinyl, 2-butinyl, 3-butinyl, isobutinyl, n-2,4-pentadiinyl, 3-methyl-2-butinyl, n-2-octinyl, n-2-dodecinyl, isododecinyl.

Examples of alkoxy are methoxy, ethoxy, propoxy, isopropoxy, butoxy, isobutoxy, pentoxy, isopentoxy, hexoxy, heptoxy or octoxy.

$C_7$-$C_9$phenylalkyl is for example benzyl, α-methylbenzyl, α,α-dimethylbenzyl or 2-phenylethyl, benzyl is preferred.

$C_5$-$C_{12}$cycloalkyl is for example cyclopentyl, cyclohexyl, cycloheptyl, methylcyclopentyl or cyclooctyl.

$C_5$-$C_{12}$cycloalkenyl is for example 3-cyclopentenyl, 3-cyclohexenyl or 3-cycloheptenyl.

Examples of a monocarboxylic acid having up to 18 carbon atoms are formic acid, acetic acid, propionic acid, the isomers of valeric acid, methyl ethyl acetic acid, trimethyl acetic acid, capronic acid, lauric acid or stearic acid. Examples for unsaturated aliphatic acids are acrylic acid, methacrylic acid, crotonic acid, linolic acid and oleic acid.

Typical examples of cycloaliphatic carboxylic acids are cyclohexane carboxylic acid or cyclopentane carboxylic acid.

Examples of aromatic carboxylic acids are benzoic acid, salicylic acid or cinnamic acid. Halogen is F, Cl, Br or I.

$C_1$-$C_{18}$alkylene is a branched or unbranched radical, for example methylene, ethylene, propylene, trimethylene, tetramethylene, pentamethylene, hexamethylene, heptamethylene, octamethylene, decamethylene or dodecamethylene.

$C_2$-$C_{12}$alkylene bridges interrupted by at least one O atom are, for example, —$CH_2$—O—$CH_2$—$CH_2$, —$CH_2$—O—$CH_2$—$CH_2$—$CH_2$, —$CH_2$—O—$CH_2$—$CH_2$—$CH_2$—$CH_2$—, —$CH_2$—O—$CH_2$—$CH_2$—O—$CH_2$—.

Alkoxycarbonyl is for example methoxycarbonyl, ethoxycarbonyl, propoxycarbonyl.

Preferably $R_1$, $R_2$, $R_3$, $R_4$ are methyl, or $R_1$ and $R_3$ are ethyl and $R_2$ and $R_4$ are methyl, or $R_1$ and $R_2$ are ethyl and $R_3$ and $R_4$ are methyl.

For instance $R_5$ is hydrogen or methyl.

In particular $R'_6$ is hydrogen and $R_6$ is H, $OR_{10}$, $NR_{10}R_{11}$, —O—C(O)—$R_{10}$ or $NR_{11}$—C(O)—$R_{10}$;

$R_{10}$ and $R_{11}$ independently are hydrogen, $C_1$-$C_{18}$alkyl, $C_2$-$C_{18}$alkenyl, $C_2$-$C_{18}$alkinyl or $C_2$-$C_{18}$alkyl which is substituted by at least one hydroxy group or, if $R_6$ is $NR_{10}R_{11}$, taken together, form a $C_2$-$C_{12}$alkylene bridge or a $C_2$-$C_{12}$-alkylene bridge interrupted by at least one O atom; or $R_6$ and $R'_6$ together are both hydrogen, a group =O or =N—O—$R_{20}$ wherein $R_{20}$ is H or straight or branched $C_1$-$C_{18}$alkyl.

In another preferred embodiment of the invention $R_6$ and $R'_6$ together form one of the bivalent groups —O—C($R_{21}$)($R_{22}$)—CH($R_{23}$)—O—, —O—CH($R_{21}$)—CH$_{22}$—C($R_{22}$)($R_{23}$)—O—, —O—CH($R_{22}$)—CH$_2$—C($R_{21}$)($R_{23}$)—O—, —O—CH$_2$—C($R_{21}$)($R_{22}$)—CH($R_{23}$)—O— and $R_{21}$, $R_{22}$ and $R_{23}$ have the meaning as defined above.

In a first step a polysiloxane is prepared, for example by ring opening of a cyclic siloxane.

Polysiloxanes with hydrogen end groups or with pending hydrogen atoms at the polymer backbone are known and commercially available. Methods for reacting hydrogen groups with unsaturated double bonds are known as hydrosililation and for example described in Advances in Organometallic Chemistry, vol. 17 pages 407-447, 1979.

During the hydrosylilation process an alkoxyamine having for example an allyl functionality in particular a compound of formula II, is added and a polysiloxane having attached the alkoxyamine at both ends or along the polysiloxane backbone is obtained. Depending on the process conditions and the amount of alkoxyamine added, comb polymers with more than two pendent alkoxyamine groups are obtained.

In a second step the alkoxyamine terminated polysiloxane is further reacted with an unsaturated monomer. Examples of unsaturated monomers are ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides or vinylidene halides.

Preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide, methacrylamide or dimethylaminopropyl-methacrylamide.

Particularly preferred are styrene, methylacrylate, ethylacrylate, butylacrylate, isobutylacrylate, tert. butylacrylate, methyl(meth)acrylate, ethyl(meth)acrylate and the isomers of butyl(meth)acryl ate.

Also subject of the invention is the triblock-copolymer or graft-copolymer itself obtained via controlled free radical polymerization according to the above mentioned process.

The compounds of formula II are novel. They may be prepared in analogy to the epoxy-functional compounds described in WO 99/46261, WO 02/48109 or U.S. Pat. No. 5,721,320. The hydroxy functional intermediate described in the afore mentioned documents is for example reacted with allyl bromide to obtain the title compounds.

Consequently a further aspect of the invention is a compound of formula II

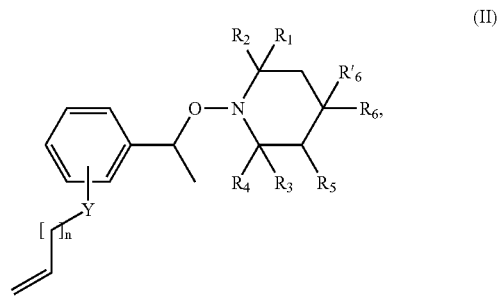

wherein
Y is a direct bond, O, NH, C(O)O or S;
n is a a number from 0-18.
$R_1$, $R_2$, $R_3$ and $R_4$ are independently of each other $C_1$-$C_4$alkyl;
$R_5$ is hydrogen or $C_1$-$C_4$alkyl;
$R'_6$ is hydrogen and $R_6$ is H, $OR_{10}$, $NR_{10}R_{11}$, —O—C(O)—$R_{10}$ or $NR_{11}$—C(O)—$R_{10}$;
$R_{10}$ and $R_{11}$, independently are hydrogen, $C_1$-$C_{18}$alkyl, $C_2$-$C_{18}$alkenyl, $C_2$-$C_{18}$alkinyl, or $C_2$-$C_{18}$alkyl which is substituted by at least one hydroxy group or, if $R_6$ is $NR_{10}R_{11}$, taken together, form a $C_2$-$C_{12}$alkylene bridge or a $C_2$-$C_{12}$-alkylene bridge interrupted by at least one O atom; or $R_6$ and $R'_6$ together are both hydrogen, a group =O or =N—O—$R_{20}$ wherein $R_{20}$ is H, straight or branched $C_1$-$C_{16}$alkyl, $C_3$-$C_{18}$alkenyl or $C_3$-$C_{18}$alkinyl, which may be unsubstituted or substitued, by one or more OH, $C_1$-$C_8$alkoxy, carboxy, $C_1$-$C_8$alkoxycarbonyl;
$C_5$-$C_{12}$cycloalkyl or $C_5$-$C_{12}$cycloalkenyl;
phenyl, $C_7$-$C_9$phenylalkyl or naphthyl which may be unsubstituted or substituted by one or more $C_1$-$C_8$alkyl, halogen, OH, $C_1$-$C_8$alkoxy, carboxy, $C_1$-$C_8$alkoxycarbonyl;
—C(O)—$C_1$-$C_{36}$alkyl, or an acyl moiety of a α,β-unsaturated carboxylic acid having 3 to 5 carbon atoms or of an aromatic carboxylic acid having 7 to 15 carbon atoms;
—SO$_3^-$Q$^+$, —PO(O$^-$Q$_+$)$_2$, —P(O)(OR$_2$)$_2$, —SO$_2$—R$_2$, —CO—NH—R$_2$, —CONH$_2$, COOR$_2$, or Si(Me)$_3$, wherein Q$^+$ is H$^+$, ammmonium or an alkali metal cation; or $R_6$ and $R_6$' are independently —O—$C_1$-$C_{12}$alkyl, —O—$C_3$-$C_{12}$alkenyl, —O—$C_3$-$C_{12}$alkinyl, —O—$C_5$-$C_8$cycloalkyl, —O-phenyl, —O-naphthyl, —O—$C_7$-$C_9$phenylalkyl; or $R_6$ and $R'_6$ together form one of the bivalent groups —O—C($R_{21}$)($R_{22}$)—CH($R_{23}$)—O—, —O—CH($R_{21}$)—CH$_{22}$—C($R_{22}$)($R_{23}$)—O—, —O—CH($R_{22}$)—CH$_2$—C($R_{21}$)($R_{23}$)—O—, —O—CH$_2$—C($R_{21}$)($R_{22}$)—CH($R_{23}$)—O—, —O-o-phenylene-O—, —O-1,2-cyclohexyliden-O—, —O---CH$_2$—CH=CH—CH$_2$—O— or

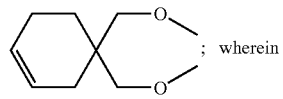

; wherein $R_{21}$ is hydrogen, $C_1$-$C_{12}$alkyl, COOH, COO—($C_1$-$C_{12}$)alkyl or CH$_2$OR$_{24}$;
$R_{22}$ and $R_{23}$ are independently hydrogen, methyl ethyl, COOH or COO—($C_1$-$C_{12}$)alkyl; and $R_{24}$ is hydrogen, $C_1$-$C_{12}$alkyl, benzyl, or a monovalent acyl residue derived from an aliphatic, cycloaliphatic or aromatic monocarboxylic acid having up to 18 carbon atoms.

Examples and preferences for the individual substituents have already been given, they apply also for the compounds.

Yet further aspects of the invention are a composition wherein the triblock-copolymer or graft-copolymer is prepared via controlled free radical polymerization according to the process described above and the use of a triblock-copolymer or graft graft-copolymer as additive for enhancing the melt flow of thermoplastic polymers during processing.

The following examples illustrate the invention.

A) Synthesis of Functional Alkoxyamine

EXAMPLE 1

Compound 101

15 g (51 mmol) 1-[1-(4-hydroxy-phenyl)-ethoxy]-2,2,6,6-tetramethyl-piperidin-4-ol prepared as described in WO 02/48109, 14 g (102 mmol) $K_2CO_3$, 8.6 ml (102 mmol) allylbromide and 50 ml acetone are refluxed for 12 hours. The reaction mixture is filtered and the solvent removed by evaporation. The residue is recrystallized from 20 ml pentane. 11.3 g (66.4%) of compound 101 are obtained as white crystals with a melting point of 66-67° C.

| Compound No. | Structure |
|---|---|
| 101 | (structure with OH, piperidine ring with N-O, phenyl, and allyloxy group) |

Elemental Analysis: Calculated $C_{20}H_{31}NO_3$; C, 72.03%; H, 9.37%; N, 4.20%; Found: C, 71.46%; H, 9.36%; N, 4.27%.

B) Synthesis of the NOR Terminated Polysiloxane

Two commercial Polysiloxane are modified in a hydrosylilation reaction in the presence of compound 101. A NOR terminated polysiloxane of the type B-C-B and a grafted polysiloxane of the type C-B(n) is obtained.

C) Synthesis of Block Copolymer B-C-B of Example 1 to 4

In a dry, argon-purged Schienk tube, the NOR terminated polysiloxane is dissolved in a tenfold amount of freshly distilled styrene. The solution is degassed in three consecutive freeze-thaw-cycles and then purged with Argon. The stirred mixture is immersed in an oil bath and polymerized at 130° C. for 24 hours. After polymerization, residual monomer is removed under vacuum at 60° C. The final block copolymer is dried at 60° C. in vacuum until constant weight is achieved.

Molecular weight and molecular weight distributions are determined by size exclusion chromatography (SEC) on an HP 1090 liquid chromatograph (software: winGPC/Polymer Standard Services, Mainz, Germany) using THF as eluent and a column combination calibrated with narrow polystyrene standards (Polymer Laboratories). The results are shown in Table 1.

TABLE 1

| blockcopolymer of example | starting material | [g] | styrene [g] | conv. [%] | $M_w$ | PD |
|---|---|---|---|---|---|---|
| PS-PSi-PS (ex. 1, 3) | NO-term-polysiloxane | 5.0 | 50 | 67.6 | 7100 | 4.8 |
| PS-graft-PSi (ex. 2, 4) | NO-graft-polysiloxane | 5.0 | 50 | 53.1 | 8000 | 1.7 |

Processing and Testing Conditions

The synthesized block copolymers described above are blended with crystal polystyrene and injection molded to a spiral (dimension: 1.5 mm) where the length of the spiral is used as measure of flowability. In addition the transparency of the injection molded spirals is inspected visually. The results of improved melt flow and transparency of the inventive examples are listed in Table 2.

| Arburg 270-210-500 | |
|---|---|
| Cylinder Temp. Zone: | 200–220° C. |
| Temp. Dye: | 220° C. |
| Mould Temperature: | 55° C. |
| Mould Cooling Time: | 10 sec. |
| Injection Time: | 0.1–0.2 sec. |
| Screw Speed: | 150 U/min |
| Back Pressure: | 55 bar |
| Back Pressure Time: | 10 sec. |
| Injection Pressure: | 1000 bar |

TABLE 2

| | additive | melt flow increase [%] | [%] | aspect |
|---|---|---|---|---|
| comparative example 1 | without | 0 | 0 | transparent, colorless |
| comparative example 2 | Tegomer ® v-si 2250 | 1.0 | 5.3 | white, opaque, inhomogeneous |
| comparative example 3 | Tegomer ® h-si 6440 | 1.0 | 0.3 | white, opaque |
| comparative example 4 | polysiloxane block of example 1 | 1.0 | 3.2 | opaque, brownish |
| comparative example 5 | polysiloxane block of example 2 | 1.0 | not processible | |
| comparative example 6 | Tegomer ® h-si 6440 | 2.0 | 7.7 | white, opaque |

TABLE 2-continued

| | additive | melt flow increase [%] | [%] | aspect |
|---|---|---|---|---|
| comparative example 7 | Tegomer ® v-si 2250 | 2.0 | 5.0 | white, opaque, inhomogeneous |
| example 1 | ps-polysiloxane-ps blockcopolymer | 1.0 | 1.2 | transparent colorless |
| example 2 | polysiloxane-graft-ps | 1.0 | 5.0 | transparent colorless |
| example 3 | ps-polysiloxane-ps blockcopolymer | 2.0 | 3.2 | transparent colorless |
| example 4 | polysiloxane-graft-ps | 2.0 | 6.2 | transparent colorless |

In contrast to commercial available Polysiloxanes of the comparative examples, the inventive examples show enhancement of melt flow and at the same time excellent compatibility proven by a colorless transparent product. Glass tranistion temperature of PS is 373 K, of Polydimethylsiloxane 146 K

The invention claimed is:

1. A composition comprising
A) a thermoplastic polymer and
B1) a triblock-copolymer of the formula B-C-B; or
B2) a graft copolymer wherein a polymer block B is grafted onto a polymer C to form a comb copolymer of idealized formula C-B(n) wherein n is greater than 2;
wherein
the polymer block B is compatible to the thermoplastic polymer A); and
the polymer block C is a polysiloxane which has a glass transition temperature of at least 20° K. below the glass transition temperature of the thermoplastic polymer A);
and the average molecular weight $M_w$ of the triblock-copolymer B1) or grafted comb copolymer B2) is below 50 000,
and wherein the triblock copolymer or the graft copolymer is prepared via controlled free radical polymerization comprising the steps
a) reacting a polysiloxane, in the presence of a functional alkoxyamine of formula (I)

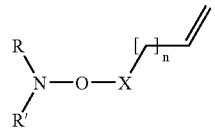

(I)

under hydrosylilation conditions and
b) reacting the resulting alkoxyamine modified polysiloxane with an ethylenically unsaturated monomer at a temperature between 60 and 160° C., wherein
X represents a group having at least one carbon atom and is such that the free radical

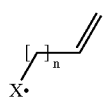

is capable of initiating polymerization of ethylenically unsaturated monomers,
n is a number from 0-18;

R and R' are independently tertiary bound $C_4$-$C_{28}$alkyl groups which are unsubstituted or substitituted by one or more electron withdrawing groups or by phenyl; or
R and R' together form a 5 or 6 membered heterocyclic ring which is substituted at least by 4 $C_1$-$C_4$alkyl groups and which may be interrupted by a further nitrogen or oxygen atom.

2. A composition according to claim 1 wherein the thermoplastic polymer A is selected from the group consisting of polyethylene, polypropylene, polystyrene, polyacrylate, polymethacrylate, polyvinylchloride, polyphenyleneoxide, polyvinylacetate, polyamide and polyester.

3. A composition according to claim 1 wherein the polymer block B is selected from the group consisting of polyisoprene, polybutadiene, polystyrene polymethacrylate and polyacrylate.

4. A composition according to claim 1 wherein the thermoplastic polymer A and the triblock-copolymer B-C-B are
polystyrene polystyrene-polysiloxane-polystyrerie,
polyethylene polyisoprene-polysiloxane-polyisoprene,
polypropylene polyisoprene-polysiloxane-polyisoprene,
polymethylmethacrylate polymethylacrylate-polysiloxane-polymethylacrylate,
polyamide polyethylacrylate-polysiloxane-polyethylacrylate,
polyester polyethylacrylate-polysiloxane-polyethylacrylate,
polyvinylchloride polyethylacrylate-polysiloxane-polyethylacrylate,
polyvinylchloride poly-n-butylacrylate-polysiloxane-poly-n-butylacrylate,
polyphenyleneoxide polystyrene-polysiloxane-polystyrene or
polyvinylacetate polymethylacrylate-polysiloxane-polymethylacrylate.

5. A composition according to claim 1 wherein the glass transition temperature of the polymer block C is 50° K. below the glass transition temperature of the thermoplastic polymer A.

6. A composition according to claim 1 wherein the average molecular weight $M_w$ of the triblock-copolymer or graft-copolymer is below 30000.

7. A composition according to claim 1 wherein the triblock-copolymer or graft copolymer is present in an amount of from 0.1 to 10% by weight, based on the weight of the thermoplastic polymer A.

8. A process for enhancing the melt flow of a thermoplastic polymer during processing, which process comprises
adding a triblock-copolymer or graft copolymer according to claim 1 to a thermoplastic polymer and processing the polymer.

* * * * *